United States Patent
Cooper et al.

(10) Patent No.: US 6,818,417 B2
(45) Date of Patent: *Nov. 16, 2004

(54) METHOD FOR LOCATING HIDDEN MICROORGANISM CONTAMINATED SURFACES IN INDUSTRIAL WATER SYSTEMS

(75) Inventors: Andrew J. Cooper, Oswego, IL (US); Michael V. Enzien, Lisle, IL (US); Steven R. Hatch, Naperville, IL (US); Bosco P. Ho, Lombard, IL (US); May M. Wu, Lisle, IL (US)

(73) Assignee: Nalco Company, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/213,682

(22) Filed: Aug. 6, 2002

(65) Prior Publication Data

US 2004/0029211 A1 Feb. 12, 2004

(51) Int. Cl.[7] .............................. C12Q 1/02; C12Q 1/06; C02F 1/00; G01N 33/533; C07K 16/12
(52) U.S. Cl. .......................... 435/29; 210/708; 435/39; 436/529; 436/531; 436/546; 436/800; 530/391.3; 530/391.5; 530/402
(58) Field of Search .......................... 210/708; 435/29, 435/39; 436/529, 531, 546, 800; 530/391.3, 391.5, 402

(56) References Cited

U.S. PATENT DOCUMENTS 6,130,101 A * 10/2000 Mao et al. ................... 436/546
6,329,165 B1 * 12/2001 Chattoraj et al. ............. 435/29
2002/0042092 A1 * 4/2002 Banks et al. ................. 435/39

OTHER PUBLICATIONS

"Diffusion and binding measurements within oral biofilms using fluorescence photobleaching recovery methods", J.J. Birmingham, N.P. Hughes, R. Treloar, Unilever Research Port Sunlight Laboratory, Phil. Trans. The Royal Society, London, 350, pp. 325–343, 1995.

Handbook of Fluorescent Probes and Research Chemicals, R.P. Haugland, Sixth Edition, Molecular Probes, Inc., pp. 22–26, 1996.

* cited by examiner

Primary Examiner—Ralph Gitomer
Assistant Examiner—Kailash C. Srivastava
(74) Attorney, Agent, or Firm—Thomas M. Breininger

(57) ABSTRACT

A method for locating hidden microorganism contaminated surfaces in industrial water systems is described and claimed. The method works by applying a solution or dispersion of a fluorogenic reagent in water to the hidden water contact surfaces of said industrial water system and allowing said fluorogenic reagent to react with any hidden microorganisms present, wherein said fluorogenic reagent is selected from the group of fluorogenic reagents that are known to react with microorganisms such that a fluorescent signal of said fluorogenic reagent is detectable in such a way as to make the detection of the fluorescent signal indicate that there are hidden microorganisms present on the water contact surfaces of the equipment and piping.

13 Claims, No Drawings

METHOD FOR LOCATING HIDDEN MICROORGANISM CONTAMINATED SURFACES IN INDUSTRIAL WATER SYSTEMS

FIELD OF THE INVENTION

This invention is in the field of industrial water systems. Specifically, this invention is in the field of locating hidden microorganism contaminated surfaces in industrial water systems.

BACKGROUND OF THE INVENTION

Throughout the world, there are many different types of industrial water systems. In the vast majority of these industrial water systems, growth of microorganisms is a problem. Microorganisms can grow in extremely diverse environmental conditions. Although many microorganisms grow at moderate temperatures from about 30° C. to about 50° C., there are other microorganisms known as phychrophiles that grow at temperatures from about 0° C. to about 30° C. and thermophiles that grow at temperatures from about 50° C. to greater than 90° C. In addition to this broad temperature range that permits microbial growth, microorganisms grow over a wide range of pH, osmotic pressure, nutrient concentration and oxygen concentration conditions. Given this wide range of conditions that permit growth, it is not surprising that microorganisms can exist and cause problems in the optimum operation of most industrial water systems.

Sources of microbial contamination in industrial water systems are numerous and may include, but are not limited to, air-borne contamination, water make-up, process leaks and improperly cleaned equipment. These microorganisms can establish microbial communities on any wettable or semi-wettable surface of the water system. Exopolymeric substance secreted from the microorganisms aid in the formation of biofilms as the microbial communities develop on the surface. These biofilms are complex ecosystems that establish a means for concentrating nutrients and offer protection for growth, and biofilms can accelerate scale, corrosion, and other undesirable fouling processes. Not only do biofilms contribute to reduction of system efficiencies, but they also provide an excellent environment for microbial proliferation that can include legionellae bacteria. It is therefore important that biofilms and other fouling processes be reduced to the greatest extent possible to minimize the health-related risk associated with legionellae and other water-borne pathogens.

Many different methods of cleaning biofilms from equipment and piping in industrial water systems are known. One such method, is a method of simultaneously cleaning and disinfecting an industrial water system as described and claimed in U.S. patent application Ser. No. 10/135,317 now pending. U.S. patent application Ser. No. 10/135,317 is incorporated by reference in its entirety.

In order to be most effective, all methods of cleaning biofilms require a modicum of knowledge as to where the biofilm is present. Understanding where a biofilm is present is simplified when it is possible to visibly inspect the surfaces of equipment and piping.

A common practice for the examination of heat exchangers is to use fiber optic probes with small cameras to visualize in realtime and on tape the condition of tube surfaces. Frequently scale, corrosion and microbial fouling can be detected or suspected using this type of sensing device. The fiber optic cables can be many meters long and easily extend the full length of the heat exchanger tubes. The flexibility of the cables also allows them to bend around right angle turns in pipes. By twisting the cable the camera viewing angle can be positioned a full 360 degrees. However, this technique has limitations such as the fact that it only provides visual information which can often be misleading as to the exact nature of the film or deposit. With this method it is possible to mistake water films for microbial deposits. In fact, scale and corrosion deposits are usually more clearly identified visually compared to microbial deposits.

In industrial water systems where it is not possible to visibly inspect the surfaces of equipment and piping, it is customary to provide an excess of treatment chemicals and cleaning chemicals to ensure that all biofilms are cleaned. When the surfaces of equipment and piping are not contaminated with hidden biofilm, the use of an excess of treatment chemicals and cleaning chemicals means a waste of chemicals and thus a waste of money. Therefore, it would be desirable to have a method of identifying where hidden microbiological contamination is present, so as to not have to provide an excess of treatment chemicals and cleaning chemicals when it was not necessary.

SUMMARY OF THE INVENTION

The instant claimed invention is a method for locating hidden microorganism-contaminated-surfaces in industrial water systems comprising the steps of:

a) providing an industrial water system;

b) draining the water from said industrial water system or from a targeted portion of said industrial water system;

c) applying a solution or dispersion of a fluorogenic reagent in water to the hidden water contact surfaces of said industrial water system and allowing said fluorogenic reagent to react with any hidden microorganisms present, wherein said fluorogenic reagent is selected from the group of fluorogenic reagents that are known to react with microorganisms such that a fluorescent signal of said fluorogenic reagent is detectable in such a way as to make the detection of the fluorescent signal indicate that there are hidden microorganisms present on the water contact surfaces or water condensable surfaces of the equipment and piping;

d) collecting said solution or dispersion after it has been in contact with the hidden water contact surfaces of said industrial water system;

e) providing means for measurement of the fluorescent signals of said fluorogenic reagent in the collected solution or dispersion;

f) using said means for measurement of said fluorescent signals of said fluorogenic reagent to measure the fluorescent signal of the fluorogenic reagent; and g) using the measured fluorescent signal to determine whether hidden microorganisms are present on the water contact surfaces of the equipment and piping of the industrial water system.

DETAILED DESCRIPTION OF THE INVENTION

The following terms have the indicated meanings:

"biodeposit" refers to the material present on the hidden water contact surfaces of industrial water systems that originated because of the presence of microorganisms in the water or on the surfaces of equipment in the industrial water systems. Typical biodeposits can include any, some or all of the following constituents:

living active microorganisms, living dormant microorganisms, dead microorganisms, cellular material released from dead microorganisms, and different types of extracellular substances secreted by microorganisms.

"biofilm" refers to a biodeposit that is at least a monolayer thick and that covers a defined area of the water contact surfaces of an industrial water system.

"CAS Registry No." refers to the Chemical Abstracts Service Registry number.

"EX" refers to the wavelength of the excitation light for the compound,

"EM" refers to the wavelength of the emission light for the compound,

"Molecular Probes" refers to Molecular Probes, Inc. 4849 Pitchford Avenue, Eugene, Oreg. 97402-9165, (541) 465-8300 (telephone), (541) 344-6504 (fax).

"nm" refers to nanometers,

"Protein" refers to a group of nitrogenous organic compounds that yield amino acids upon hydrolysis.

The method of the instant claimed invention can be used to locate hidden microbiological contamination on the surfaces of equipment and piping in many industrial water systems. These industrial water systems include, but are not limited to cooling water systems, including open recirculating, closed and once-through cooling water systems; boilers and boiler water systems; mineral process waters including mineral washing, flotation and benefaction; paper mill digesters, washers, bleach plants, stock chests, and white water systems, and paper machine surfaces; black liquor evaporators in the pulp industry; gas scrubbers and air washers; equipment in the recreational water industry, metal-working industry, decorative water features, continuous casting processes in the metallurgical industry; air conditioning and refrigeration systems; industrial and petroleum process water; indirect contact cooling and heating water; pasteurization water; water reclamation systems, water purification systems; membrane filtration water systems; food processing streams; waste treatment systems; clarifiers, liquid-solid applications, municipal sewage treatment, municipal water systems, potable water systems, fire protection water systems, aquifers, water tanks, sprinkler systems and water heaters.

In order to conduct the method of the instant claimed invention it is required, that the industrial water system in its entirety, or alternatively, a targeted portion of the industrial water system, such as the piece of equipment or piping of interest in the industrial water system, be drained of water. This is necessary in order to allow good contact of the solution of fluorogenic reagent with the hidden surfaces of the equipment and piping. Prior to draining the water it is recommended to stop all energy transfer within the industrial water system.

There are three major categories of fluorogenic reagents that are capable of being used in the method of the instant claimed invention. The first category are those fluorogenic reagents that have a detectable fluorescent signal; wherein the wavelength of the detectable fluorescent signal changes after said fluorogenic reagent comes into contact with microorganisms. This first category of fluorogenic reagents include resazurin, and the commercially available salts of resazurin, such as, but not limited to, resazurin, sodium salt, 4-methylumbelliferyl phosphate (abbreviated "4-MUP") and pyranine phosphate. These fluorogenic reagents are available commercially through most major chemical supply companies.

The second category of fluorogenic reagents are those fluorogenic reagents that have a weak fluorescent signal; wherein said weak fluorescent signal remains at the same wavelength, while increasing measurably in intensity after said fluorogenic reagent comes into contact with microorganisms. Fluorogenic reagents in this second category include fluorochrome-polysaccharide conjugate compositions and fluorochrome-protein conjugate compositions.

Certain of the fluorochrome-polysaccharide conjugates and fluorochrome-protein conjugates are available from a commercial fluorescent material company, such as Molecular Probes. Other conjugates must be synthesized. The basic synthesis technique involves attaching a linking group to a fluorochrome with the linking group capable of affixing either a protein or a polysaccharide to the fluorochrome or attaching a linking group to the polysaccharide or protein with this linking group capable of affixing the fluorochrome to it.

The linking groups for conjugates containing polysaccharides are the free aldehyde and ketone groups on the polysaccharide. These aldehyde and ketone groups are exposed when sugar moieties of the polysaccharide are in the open-ring configuration, which is in equilibrium with the closed ring form. Periodate oxidation of vicinal diols can also be used to expose more ketones and aldehydes in polysaccharides. Once exposed, aldehydes and ketones can be reacted with fluorochromes; wherein the preferred fluorochromes are either fluorescent hydrazines or fluorescent aromatic amines.

Polysaccharides suitable for combination with fluorochromes into fluorochrome-polysaccharide conjugates include, but are not limited to: starch, including amylose and amylopectin, dextrin, dextran and glycosaminoglycans. The more preferred polysaccharides are starch, glycogen, dextrin and dextran. The most preferred polysaccharide is starch.

Fluorochromes that are capable of reacting with the ketones and aldehydes in polysaccharides include fluorescent hydrazines such as, but not limited to,:

fluorescein-5-thiosemicarbazide {CAS Registry No. 76863-28-0}, 5-(((2-(carbohydroazino) methyl)thio)acetyl) aminofluorescein, BODIPY® FL hydrazide {CAS Registry No. 178388-71-1}, BODIPY® 530/550 hydrazide, Texas Red® hydrazide {CAS Registry No. 140681-85-2}, Cascade Blue® hydrazide trisodium salt {CAS Registry No. 137182-38-8},
1-pyrenebutanoic acid hydrazide {CAS Registry No. 55486-13-0},
7-diethylaminocoumarin-3-carboxylic acid hydrazide,
dansyl hydrazide {CAS Registry No. 33008-06-9}, and
lucifer yellow CH lithium salt {CAS Registry No. 67769-47-5}.

The preferred fluorochromes that are fluorescent hydrazines are:

5-(((2-(carbohydroazino) methyl)thio)acetyl) aminofluorescein,
BODIPY® 530/550 hydrazide,
Texas Red® hydrazide,
Cascade Blue® hydrazide trisodium salt,
7-diethylaminocoumarin-3-carboxylic acid hydrazide, and
lucifer yellow CH lithium salt.

The most highly preferred of these fluorescent hydrazine fluorochromes are

BODIPY® 530/550 hydrazide{EX534,EM551},
Texas Red® hydrazide {EX584, EM605},
Cascade Blue® hydrazide trisodium salt {EX399, EM421},
7-diethylaminocoumarin-3-carboxylic acid hydrazide {EX420, EM468}, and
lucifer yellow CH lithium salt {EX428, EM536}.

Fluorochromes that are fluorescent aromatic amines that are capable of reacting with the ketones and aldehydes in polysaccharides include:

2-aminoacridone hydrochloride,
5-aminofluorescein {CAS Registry No. 51649-83-3},
BODIPY® FL EDA,
BODIPY® 530/550 EDA,
Texas Red® cadaverine {CAS Registry No. 203866-87-9},
Cascade Blue® ethylenediamine trisodium salt {CAS Registry No. 138039-52-8},
1-pyrenepropylamine hydrochloride,
7-amino-4-methylcoumarin {CAS Registry No. 26093-31-2},
dansyl ethylenediamine {CAS Registry No. 35060-08-3}, and
lucifer yellow ethylenediamine.

The preferred fluorochromes that are aromatic amines are:
2-aminoacridone hydrochloride,
5-aminofluorescein,
BODIPY® FL EDA,
BODIPY® 530/550 EDA,
Texas Red® cadaverine,
Cascade Blue® ethylenediamine trisodium salt,
1-pyrenepropylamine hydrochloride,
7-amino-4-methylcoumarin,
dansyl ethylenediamine, and
lucifer yellow ethylenediamine.

The more preferred aromatic amine fluorochromes are
2-aminoacridone hydrochloride,
5-aminofluorescein,
BODIPY® FL EDA,
BODIPY® 530/550 EDA,
Texas Red® cadaverine,
Cascade Blue® ethylenediamine trisodium salt,
lucifer yellow ethylenediamine.

The most preferred aromatic amine fluorochromes are
5-aminofluorescein {EX488, EM518},
Cascade Blue® ethylenediamine trisodium salt {EX399, EM423} and
lucifer yellow ethylenediamine {EX425, EM522}.

The preferred fluorochromes were selected based on their wavelength of excitation (with preference given to those capable of being excited by visible light), the intensity of their detectable fluorescent signal and their photostability. All the listed fluorescent hydrazines and aromatic amines can be purchased from Molecular Probes.

A suitable synthesis route for making fluorochrome-polysaccharide conjugates is as follows: one of the fluorochromes from the above list is combined with and allowed to react with the exposed aldehydes or ketones present on the polysaccharide. In conducting this reaction, the mole ratio of fluorochrome to polysaccharide should be at a minimum of from about 2:1, preferably from about 10–50:1. The conjugation reaction usually takes from about 12 to about 24 hours. After conjugation the fluorochrome-polysaccharide conjugate usually requires purification. The conjugate can be purified from un-reacted fluorochrome using a suitable separation technique, such as size exclusion chromatography.

The fluorescent signal of each eluant fraction collected from the size exclusion chromatography should be measured at the appropriate excitation and emission wavelength for the fluorochrome. The fractions with the weakest fluorescent signal upon manufacture and the strongest fluorescent signal after reaction with microorganisms are preferable for use as a fluorogenic reagent in the method of the instant claimed invention. This is because contacting this conjugate with microorganisms will cause biodegradation of the polysaccharide polymer in such a way as to permit the fluorescent signal of the fluorochrome to be detectable. The fluorescent signal will increase proportionally to the amount of biodegradation of the polysaccharide, because more biodegradation exposes more of the fluorochrome.

The preferred fluorochrome-polysaccharide conjugates with fluorochromes that are hydrazines, for use in the method of the instant claimed invention are:

fluorescein-5-thiosemicarbazide-starch,
5-thiosemicarbazide-dextran,
5-thiosemicarbazide-dextrin,
5-thiosemicarbazide-glycogen,
5-(((2-(carbohydroazino) methyl)thio)acetyl) amonofluorescein-starch,
5-(((2-(carbohydroazino) methyl)thio)acetyl) amonofluorescein-dextran,
5-(((2-(carbohydroazino) methyl)thio)acetyl) amonofluorescein-dextrin,
5-(((2-(carbohydroazino) methyl)thio)acetyl) amonofluorescein-glycogen,
BODIPY® FL hydrazide-starch,
BODIPY® FL hydrazide-dextran,
BODIPY® FL hydrazide-dextrin, BODIPY® FL hydrazide-glycogen,
BODIPY® 530/550 hydrazide-starch,
BODIPY® 530/550 hydrazide-dextran,
BODIPY® 530/550 hydrazide-dextrin,
BODIPY® 530/550 hydrazide-glycogen,
Texas Red® hydrazide-starch,
Texas Red® hydrazide-dextran,
Texas Red® hydrazide-dextrin,
Texas Red® hydrazide-glycogen,
Cascade Blue® hydrazide trisodium salt-starch,
Cascade Blue® hydrazide trisodium salt-dextran,
Cascade Blue® hydrazide trisodium salt-dextrin,
Cascade Blue® hydrazide trisodium salt-glycogen,
1-pyrenebutanoic acid hydrazide-starch,
1-pyrenebutanoic acid hydrazide-dextran,
1-pyrenebutanoic acid hydrazide-dextrin,
1-pyrenebutanoic acid hydrazide-glycogen,
7-diethylaminocoumarin-3-carboxylic acid hydrazide-starch,
7-diethylaminocoumarin-3-carboxylic acid hydrazide-dextran,
7-diethylaminocoumarin-3-carboxylic acid hydrazide-dextrin,
7-diethylaminocoumarin-3-carboxylic acid hydrazide-glycogen,
dansyl hydrazide-starch,
dansyl hydrazide-dextran,
dansyl hydrazide-dextrin,
dansyl hydrazide-glycogen,
lucifer yellow CH lithium salt-starch,
lucifer yellow CH lithium salt-dextran,
lucifer yellow CH lithium salt-dextrin, and
lucifer yellow CH lithium salt-glycogen.

Fluorochrome-Protein conjugates capable of being used in the method of the instant claimed invention are either available commercially from Molecular Probes or capable of being synthesized by techniques known to ordinary people in the art of organic chemistry.

Proteins suitable for use in the fluorochrome-protein conjugates include simple proteins such as albumins, including, ovalbumin, lactalbumin and bovine serum albumin {CAS Registry No. 9048-46-8}, casein, globulins, glutelins, prolamines, albuminoids, histones, soy proteins and protamines;

conjugated proteins such as nucleoproteins, glycoproteins, phosphoproteins, hemoglobins, lecithoproteins and lipoproteins; and derived proteins such as proteans, metaproteins, coagulated proteins, proteoses, peptones and peptides.

The preferred protein to use in the fluorochrome-protein conjugates is selected from the group consisting of albumins, casein and soy protein. The more preferred protein to use in the fluorochrome-protein conjugates is selected from the group consisting of albumins. The most preferred protein is to use in the fluorochrome-protein conjugates is bovine serum albumin {abbreviated "BSA"}.

Although diverse in origin and in primary, secondary, and tertiary structure, all proteins contain amines ($-NH_2$). These amine groups, which are universally present in proteins, can be reacted with fluorochromes that are known to be reactive with amines. In this way fluorochrome-protein conjugates suitable for use with the instant claimed invention can be synthesized.

There are three major classes of fluorochromes that can be used to react with the amines on proteins to create fluorochrome-protein conjugates. These are succinimidyl esters, including sulfosuccinimidyl esters, isothiocyanates, and sulfonyl chlorides. Other fluorochromes that are know to react with the amines on proteins include dichlorotriazines, aryl halides, acyl azides, and 4-sulfo-2,3,5,6-tetrafluorophenyl ester groups.

Suitable fluorochromes capable of reacting with the amine groups on proteins are shown in Table I. Each of these compounds is available from Molecular Probes.

TABLE I

Fluorochromes capable of reacting with the amine groups on proteins

| excitation (EX) and emission (EM) maxima (in nm) EX/EM | Fluorochromes |
|---|---|
| 524/544 | eosin-5-isothiocyanate |
| 530/555 | erythrosin-5-isothiocyanate |
| 494/518 | fluorescein-5-isothiocyanate |
| | fluorescein-6-isothiocyanate |
| | 5-carboxyfluorescein, succinimidyl ester |
| | 6-carboxyfluorescein, succinimidyl ester |
| | 5-(and-6)-carboxyfluorescein, succinimidyl ester |
| | 6-(fluorescein-5-carboxamido)hexanoic acid, succinimidyl ester |
| | 6-(fluorescein-5-(and-6)-carboxamido)hexanoic acid, succinimidyl ester |
| | 6-(fluorescein-5-(and-6)-carboxamido)hexanoic acid, succinimidyl ester |
| | fluorescein-5-EX, succinimidyl ester |
| | 5-carboxyfluorescein-bis-(5-carboxymethoxy-2-nitrobenzyl)ether, -alanine-carboxamide, succinimidyl ester |

TABLE I-continued

Fluorochromes capable of reacting with the amine groups on proteins

| excitation (EX) and emission (EM) maxima (in nm) EX/EM | Fluorochromes |
|---|---|
| 535/556 | 6-carboxy-2',4,4',5',7,7'-hexachlorofluorescein, succinimidyl ester |
| 520/548 | 6-carboxy-4',5'-dichloro-2',7'-dimethoxyfluorescein, succinimidyl ester |
| 496/524 | Oregon Green ® 488 carboxylic acid, succinimidyl ester |
| | Oregon Green ® 488 isothiocyanate |
| 511/530 | Oregon Green ® 514 carboxylic acid, succinimidyl ester |
| 502/527 | Rhodamine Green ™ carboxylic acid, succinimidyl ester |
| | Rhodamine Green ™ carboxylic acid, trifluoroacetamide, succinimidyl ester |
| | Rhodamine Green ™-X, succinimidyl ester |
| 528/544 | 5-carboxy-2',4',5',7'-tetrabromosulfonefluorescein, succinimidyl ester, bis-(diisopropylethylammonium)salt |
| 521/536 | 6-carboxy-2,4,7,7'-tetrachlorofluorescein, succinimidyl ester |
| 500/506 | 4,4-difluoro-1,3,5,7-tetramethyl-4-bora-3a,4a-diaza-s-indacene-8-propionic acid, succinimidyl ester |
| 505/513 | 4,4-difluoro-5,7-dimethyl-4-bora-3a,4a-diaza-s-indacene-3-propionic acid, succinimidyl ester |
| | 4,4-difluoro-5,7-dimethyl-4-bora-3a,4a-diaza-s-indacene-3-propionic acid, sulfosuccinimidyl ester |
| | N-(4,4-difluoro-5,7-dimethyl-4-bora-3a,4a-diaza-s-indacene-3-propionyl)cysteic acid, succinimidyl ester |
| | 6-((4,4-difluoro-5,7-dimethyl-4-bora-3a,4a-diaza-s-indacene-3-propionyl)amino)hexanoic acid, succinimidyl ester |
| | 4,4-difluoro-5,7-dimethyl-4-bora-3a,4a-diaza-s-indacene-3-pentanoic acid, succinimidyl ester |
| 528/550 | 4,4-difluoro-5-phenyl-4-bora-3a,4a-diaza-s-indacene-3-propionic acid, succinimidyl ester |
| 534/554 | 4,4-difluoro-5,7-diphenyl-4-bora-3a,4a-diaza-s-indacene-3-propionic acid, succinimidyl ester |
| 542/574 | 6-((4,4-difluoro-1,3-dimethyl-5-(4-methoxyphenyl)-4-bora-3a,4a-diaza-s-indacene-2-propionyl)amino)hexanoic acid, succinimidyl ester |
| 558/569 | 4,4-difluoro-5-(2-thienyl)-4-bora-3a,4a-diaza-s-indacene-3-propionic acid, succinimidyl ester |
| 565/571 | 4,4-difluoro-5-styryl-4-bora-3a,4a-diaza-s-indacene-3-propionic acid, succinimidyl ester |
| 576/590 | 4,4-difluoro-5-(2-pyrrolyl)-4-bora-3a,4a-diaza-s-indacene-3-propionic acid, succinimidyl ester |
| 584/592 | 4,4-difluoro-5-(4-phenyl-1,3-butadienyl)-4-bora-3a,4a-diaza-s-indacene-3-propionic acid, succinimidyl ester |
| 589/617 | 6-(((4-(4,4-difluoro-5-(2-thienyl)-4-bora-3a,4a-diaza-s-indacene-3-yl)phenoxy)acetyl)amino)hexanoic acid, succinimidyl ester |
| 625/640 | 6-(((4,4-difluoro-5-(2-thienyl)-4-bora-3a,4a-diaza-s-indacene-3-yl)styryloxy)acetyl)aminohexanoic acid, succinimidyl ester |
| 646/660 | 6-(((4,4-difluoro-5-(2-pyrrolyl)-4-bora-3a,4a-diaza-s-indacene-3-yl)styryloxy)acetyl)aminohexanoic acid, succinimidyl ester |
| 570/590 | Lissamine ™ rhodamine B sulfonyl chloride |
| 602/672 | 5-(and-6)-carboxynaphthofluorescein, succinimidyl ester |
| 525/555 | 5-carboxyrhodamine 6G, succinimidyl ester |
| | 6-carboxyrhodamine 6G, succinimidyl ester |
| | 5-(and-6)-carboxyrhodamine 6G, succinimidyl ester |
| 580/590 | Rhodamine Red ™-X, succinimidyl ester |
| 555/580 | 5-carboxytetramethylrhodamine, succinimidyl ester |
| | 6-carboxytetramethylrhodamine, succinimidyl ester |
| | 5-(and-6)-carboxytetramethylrhodamine, succinimidyl ester |
| | 6-(tetramethylrhodamine-5-(and-6)-carboxamido)hexanoic acid, succinimidyl ester |
| | tetramethylrhodamine-5-isothiocyanate |
| | tetramethylrhodamine-6-isothiocyanate |
| | tetramethylrhodamine-5-(and-6)-isothiocyanate |
| 595/615 | Texas Red ®-X, succinimidyl ester |
| | Texas Red ® sulfonyl chloride |
| 580/605 | 5-carboxy-X-rhodamine, succinimidyl ester |
| | 6-carboxy-X-rhodamine, succinimidyl ester |
| | 5-(and-6)-carboxy-X-rhodamine, succinimidyl ester |
| | X-rhodamine-5-(and-6)-isothiocyanate |
| 409/558 | Cascade Yellow ™ succinimidyl ester |
| 415/570 | 1-(3-(succinimidyloxycarbonyl)benzyl)-4-(5-(4-methoxyphenyl)oxazol-2-yl)pyridinium bromide |
| 346/442 | Alexa Fluor ® 350 carboxylic acid, succinimidyl ester |
| 365/460 | Marina Blue ® succinimidyl ester |
| 410/455 | Pacific Blue ™ succinimidyl ester |
| 433/539 | Alexa Fluor ® 430 carboxylic acid, succinimidyl ester |
| 495/519 | Alexa Fluor ® 488 carboxylic acid, succinimidyl ester |
| 532/554 | Alexa Fluor ® 532 carboxylic acid, succinimidyl ester |
| 556/573 | Alexa Fluor ® 546 carboxylic acid, succinimidyl ester |
| 555/565 | Alexa Fluor ® 555 carboxylic acid, succinimidyl ester |
| 555/580 | 5-carboxytetramethylrhodamine, succinimidyl ester |
| | 6-carboxytetramethylrhodamine, succinimidyl ester |
| | 5-(and-6)-carboxytetramethylrhodamine, succinimidyl ester |
| | 6-(tetramethylrhodamine-5-(and-6)-carboxamido)hexanoic acid, succinimidyl ester |
| 570/590 | Rhodamine Red ™-X, succinimidyl ester |
| 578/603 | Alexa Fluor ® 568 carboxylic acid, succinimidyl ester |

TABLE I-continued

Fluorochromes capable of reacting with the amine groups on proteins

| excitation (EX) and emission (EM) maxima (in nm) EX/EM | Fluorochromes |
|---|---|
| 590/617 | Alexa Fluor ® 594 carboxylic acid, succinimidyl ester |
| 632/647 | Alexa Fluor ® 633 carboxylic acid, succinimidyl ester |
| 650/668 | Alexa Fluor ® 647 carboxylic acid, succinimidyl ester |
| 663/690 | Alexa Fluor ® 660 carboxylic acid, succinimidyl ester |
| 679/702 | Alexa Fluor ® 680 carboxylic acid, succinimidyl ester |
| 702/723 | Alexa Fluor ® 700 carboxylic acid, succinimidyl ester |
| 749/775 | Alexa Fluor ® 750 carboxylic acid, succinimidyl ester |

(X) = Aminohexanoyl spacer separating the dye and succinimidyl ester.
(EX) = A seven-atom spacer that is more hydrophilic than X.

The preferred fluorochromes for use in the fluorochrome-protein conjugates are selected from the group consisting of
eosin-5-isothiocyanate,
fluorescein-5-isothiocyanate,
fluorescein-6-isothiocyanate,
5-carboxyfluorescein, succinimidyl ester,
6-carboxyfluorescein, succinimidyl ester,
5-(and-6)-carboxyfluorescein, succinimidyl ester,
6-(fluorescein-5-carboxamido)hexanoic acid, succinimidyl ester,
6-(fluorescein-5-(and -6)-carboxamido)hexanoic acid, succinimidyl ester,
fluorescein-5-EX, succinimidyl ester (where EX is a seven-atom spacer that is
more hydrophilic than X, wherein X is an aminohexanoyl spacer separating the
fluorochrome and succinimidyl ester), and
5-carboxyfluorescein-bis-(5-carboxymethoxy-2-nitrobenzyl) ether, -alanine-carboxamide, succinimidyl ester. The more preferred fluorochromes for use in the fluorochrome-protein conjugates are selected from the group consisting of eosin-5-isothiocyanate and fluorescein-5- or 6-isothiocyanate. The most preferred fluorochrome for use in the fluorochrome-protein conjugates is eosin-5-isothiocyanate.

The preferred fluorochromes were selected based on their wavelength of excitation (capable of being excited by visible light), their brightness of fluorescence and their photostability.

The mole ratio of fluorochrome to protein should be about a minimum of 2:1, and is preferably from about 10 to about 100:1. The conjugation reaction time may be completed in as little as 1 hour, or may take as long as 72 hours. After conjugation, the fluorochrome-protein conjugate is preferably purified from free fluorochrome using size exclusion chromatography (gel filtration). Sephadex™ G-25 Fine gel filtration media available from Sigma-Aldrich Corporation, St. Louis, Mo., USA, is suitable for this purpose. Other gel filtration media may be more suitable depending on the size of the protein that is being reacted.

The fluorescent signal of the fluorochrome-protein conjugate should be measured using the appropriate wavelengths for excitation and emission of the selected probe, for each eluent fraction that contains fluorochrome-protein conjugate collected from the size exclusion chromatography. The fractions exhibiting the weakest fluorescent signal upon manufacture, and the greatest fluorescent signal after reaction with microorganisms are the preferred fraction for use as the appropriate reagent in the method of the instant claimed invention.

The reason these conjugates are suitable for use in the method of the instant claimed invention is that the presence of microorganisms will cause degradation of the protein, with this degradation leading to a release of individual monomer, dimers and polypeptides that have attached fluorochromes. The fluorescent signal of these fluorochromes will increase proportionally to the biodegradation of the protein.

The preferred fluorochrome-protein conjugates for use in the method of the instant claimed invention are eosin-bovine serum albumin and fluorescein-bovine serum albumin.

In circumstances where the mere detection of the presence or absence of hidden microorganisms on the water contact surfaces of an industrial water system is not enough information, the fluorochrome-polysaccharide and fluorochrome-protein conjugate compositions can also be used to obtain a quantitative determination of biodeposits. This determination is based upon continued increase in the measured fluorescent signal of the fluorochrome-polysaccharide or fluorochrome-protein conjugate. This continued degradation is believed to be attributable to enzymes located within the biodeposit. This type of quantitative determination preferentially uses a rate calculation. This rate is typically expressed as measured fluorescent single (expressed in "fluorescent units", a dimensionless number) per unit of time. The time of exposure must be known in order to determine the rate, but the exposure time is not specified. The exposure time of the fluorochrome-protein or fluorochrome-polysaccharide to the biodeposit may vary from one second to 1 day, depending on the system and the biodeposit. The preferred time of exposure is 1 minute to 120 minutes. The most preferred exposure time is 5 minutes to 60 minutes. Several rates may also be determined by collecting samples at several different exposure times and measuring the fluorescent signal of the fluorogenic reagent in each sample.

The third category of fluorogenic reagents are those fluorogenic reagents that have a detectable fluorescent signal; wherein said detectable fluorescent signal remains at the same wavelength, but decreases measurably in intensity after said fluorogenic reagent comes into contact with biodeposits. This is because with this category of fluorogenic reagents, the fluorogenic reagents are all capable of irreversibly bonding to biodeposits; thus the more biodeposits present, the more of the fluorogenic reagent is bonded and thus, the less the intensity of the fluorescent signal of the unbonded fluorogenic reagent. Therefore, fluorogenic reagents in this third category include any fluorogenic reagent capable of bonding irreversibly to biodeposits.

A suitable fluorogenic reagent in this third category is Rhodamine Green. Rhodamine Green is available from Molecular Probes.

When the method of the instant claimed invention is used prior to an industrial water system being cleaned, any suitable fluorogenic reagent may be used. If the method is used to look for hidden microbiological contamination after the industrial water system has been cleaned, then it is recommended to use a fluorogenic reagent that is stable in the presence of bleach or other halogens, which are so often used in the cleaning and disinfecting of industrial water systems. The fluorogenic reagents that are known to be stable in the presence of oxidizing biocides are selected from the group consisting of 4-methylumbelliferyl phosphate, eosin-bovine serum albumin, and pyranine phosphate.

The solution of fluorogenic reagent is applied to the equipment and piping by any technique known to people of ordinary skill in the art of the specific industrial water system. The simplest technique is just to pour the solution into the equipment and have it flow through the equipment using gravity as the motivating force.

After the solution has been collected a fluorometer is used to detect the fluorescent signal of the flourogenic reagent. Suitable fluorometers include, but are not limited to the following:

1. Spex fluorometer available from Jobin Yvon Spex, 3880 Park Ave, Edison N.J. 08820, telephone (732) 494-8660;
2. Turner Designs TD 700, available from Turner Designs, 845 W. Maude Avenue Sunnyvale, Calif. 94085, telephone (877) 316-8049;
3. 10-AU-005-CE, available from Turner Designs, 845 W. Maude Avenue Sunnyvale, Calif. 94085, telephone (877) 316-8049; and
4. Model QM-2000-2 Steady State Spectrophotometer, available from Photon Technology International, Inc., 1009 Lenox Drive, Lawrenceville, N.J. 08648, telephone: (609) 896-0310.

There are also fluorometers available from Ondeo Nalco Company which, with some modification within the ability of people of ordinary skill in the art of fluorometry, could be used in the method of the instant claimed invention. These fluorometers that can be used with some modification include the TRASAR® 350 fluorometer, the TRASAR® 3000 fluorometer and the TRASAR®T 8000 fluorometer.

For a fluorogenic reagent, such as resazurin that has a fluorescent signal before it encounters microorganisms and a second, different fluorescent signal after it encounters microorganisms the means for measuring the fluorometric signal needs to be able to detect both the fluorescent signal of the resazurin and the fluorescent signal of resorufin, which is what resazurin turns into after it encounters microorganisms.

Once the fluorescent signal has been detected the wavelength of the signal, whether the signal is present, and if is presence or absence of the signal and the absolute amount of fluorescent signal detected is used to determine whether there is hidden microbiological contamination present in the industrial water system.

In analyzing the information it is important to understand that the nature of any biodeposit is heavily influenced by the physical and nutritional conditions in which the deposit develops. Any diagnosis or evaluation of biodeposit must acknowledge that the potential variation in biodeposit inorganic, organic, and biological composition and structural features is nearly infinite. Therefore, the instant invention does not rely upon any one biodeposit constituent or feature to enable detection of microorganisms. Rather, the fluorogenic reagent categories disclosed herein are capable of detecting a variety of biodeposit, biofilm, and microorganism activities and features. Some of these activities include enzymatic activities and cell-membrane potentials. Some of these features include the presence of proteins and carbohydrates. These activities and features are associated with any of the biodeposit constituents, including viable microorganisms, dead microorganisms, dormant microorganisms, cellular material released from dead microorganisms, and extracellular substances secreted by microorganisms.

If the test in one part of the industrial water system is negative for microorganisms but there are still believed to be microorganisms present, then the application point for the solution or dispersion of fluorogenic reagent can be moved so that a different part of the industrial water system can be contacted with the fluorogenic reagent. Then the steps of the instant claimed invention can be repeated as necessary in order to determine whether there is hidden microbiological contamination present on the water contact surfaces of interest and if there is hidden microbiological contamination present, locating where it is in the industrial water system.

With all of these fluorogenic reagents it is possible, though not required, to formulate the fluorogenic reagent with an inert tracer, wherein the inert tracer is chosen such that its fluorescent signal is detectable at a wavelength that is different than the emission wavelength of the fluorogenic reagent. Suitable inert tracers include, but are not limited to, 1,5-napthalenedisulfonic acid disodium salt (NDSA) CAS Registry No. 1655-29-4 and 1,3,6,8-pyrenetetrasulfonic acid (PTSA) CAS Registry No. 59572-10-0, which are both available from Ondeo Nalco Company, Ondeo Nalco Center, Naperville, Ill., (630) 305-1000. The purpose of the inert tracer is that with the inert tracer present it is possible, using techniques known in the art of inert tracer technology, to determine the concentration of the inert tracer in the fluorogenic reagent solution or dispersion that is collected after the solution or dispersion has been in contact with the hidden water contact surfaces of the industrial water system. Once the concentration of the inert tracer is known, it is possible to calculate how much of the fluorogenic reagent should be present in the collected solution or dispersion. Once the actual amount of fluorogenic reagent is known (by comparing the measured fluorescent signal with a standard chart relating measured fluorescent signal to concentration of fluorogenic reagent) in the collected solution or dispersion it is possible to know how much fluorogenic reagent was not collected. This information may be of considerable use to the operators of the industrial water system.

The specific examples herein disclosed are to be considered as being primarily illustrative. Various changes beyond those described, will, no doubt, occur to those skilled in the art; and such changes are to be understood as forming a part of this invention insofar as they fall within the spirit and scope of the appended claims.

The following examples are presented to be illustrative of the present invention and to teach one of ordinary skill how to make and use the invention. These examples are not intended to limit the invention or its protection in any way.

EXAMPLES

Example 1
Bioflim Detection in a Bench-scale Tubular Reactor

It is well established that in the presence of microorganism, the fluorogenic reagent, resazurin, converts to resorufin and that the detection of resorufin is indicative that the resazurin has come into contact with microorganisms.

The method of the instant claimed invention is conducted in a continuous flow bench-top tubular bioreactor equipped with an on-line data acquisition system. The reactor is made of ⅛ inch diameter tubing that is 32 feet long. The tubing simulates cooling water heat exchange tubes. The tubing is divided into two 16 foot loops in series with each tube being connected to a pressure transducer. As a comparative method, biofilm development is monitored by a pressure differential method where an increase in biofilm thickness causes an increase in differential pressure.

In order to conduct the experiment, the system is initially inoculated with a field cooling water deposit that contains *Pseudomonas aureginosa* as the dominant microbial population. The reactor is operated in a continuous flow mode. Biofouling is enhanced by adding 500 ppm of tryptic soy broth at a flow rate of 11 ml/min.

At the end of the growth test the data is collected and pressure differential results presented in Example Table 1-1, which is a comparative example.

EXAMPLE TABLE 1-1

| Elapsed time | Differential Pressure δP (psi) | | Increase in δP (psi) | |
|---|---|---|---|---|
| (hours) | Transducer 1 | Transducer 2 | Transducer 1 | Transducer 2 |
| 0 | 1.73916 | 2.00625 | | |
| 48 | 2.03388 | 2.18124 | 0.29472 | 0.17499 |

Average = 0.234855

The increase in differential pressure is attributed to the growth of the biofilm because the growth of the biofilm restricts the diameter of the pipe and that restricted diameter leads to an increase in pressure. Thus, this test, which is a comparative example, not an example of the instant claimed invention, shows that there is biofilm present in the reactor.

Resazurin, sodium salt is obtained from Aldrich. Sufficient resazurin, sodium salt is dissolved in 200 ml deionized water to make a 1 ppm fluorogenic reagent solution. Aliquot sample A is taken from the fluorogenic reagent solution. Prior to the detection test one of the tubing loops from the tubular reactor is disconnected from the system, liquid content drained and aliquot sample B is collected. The drained loop is then connected to the fluorogenic reagent solution. Fluorogenic reagent solution is recirculated through the loop with a pump at 376 ml/min for 2 min. to allow contact between microorganisms and fluorogenic reagent. An aliquot, sample C, is taken of this reacted fluorogenic reagent. Samples A, B, and C are each passed through a 0.2 μm filter to remove bacteria cells.

The fluorescent signals of resazurin and resorufin are measured with a Jobin Yvon Fluorometer at excitation 550 nm, emission 634 nm for resazurin and emission 583 nm for resorufin. The instrument is set at slit width of 2.5 nm (excitation) and 2.5 nm (emission). The fluorescent signal information is shown in Example Table 1-2.

EXAMPLE TABLE 1-2

| | Measured Fluorescence Signal | | |
|---|---|---|---|
| Sample | resorufin ($R_f$) | resazurin ($R_z$) | Ratio of $R_f/R_z$ |
| A | 166130 | 252960 | 0.66 |
| B | 2030(measured at 583 nm with no resorufin present in the water) | 1500(measured at 634 nm with no resazurin present in the water) | |
| C | 714380 | 349880 | 2.04 |

Fluorescent signal information from Example Table 1-2 showed an increase in the fluorescent signal due to the increased presence of resorufin, indicating the resazurin had contacted hidden microorganism contaminated surfaces. Therefore, the method of the instant claimed invention clearly showed the existence of biodeposits in this bench-scale tubular reactor.

Another method of analyzing this data also shows that the resazurin encountered hidden microorganism contaminated surfaces in the bench-scale tubular reactor. In this method of analyzing the data, the existence of biodeposits is detected by comparing the change in the intensity of the detected fluorescent signal of resorufin ($R_f$), resazurin ($R_z$) or the ratio of $R_f/R_z$ using the detected fluorescent signals of the unreacted fluorogenic reagent(resazurin), the reacted fluorogenic reagent (resorufin) and if necessary, it is possible to "subtract out" the measured fluorescent signal attributed to the background fluorescence of the water itself.

Example 2

Surface Detection of Microbial Activity on Various Surfaces by Filling and Pumping In this example the following Chemicals are used.

A 1% resazurin stock solution in DI (deionized) water is kept in the refrigerator for longer stable storage.

A 100 ppm resazurin solution in DI water is made from the 1% solution.

A 2 ppm resazurin solution in DI water is made from the 100 ppm solution.

The 2 ppm solution is used to measure microbial activity.

A stock of water solution is used as the diluent for further dilution of the resazurin solution to a concentration chosen to measure the fluorescent signals. Throughout this Example, the typical concentration chosen to measure the fluorescent signals is 40 ppb.

The following equipment was used and the indicated procedure was followed in this Example:

The measurement of fluorescent signal is made on a Jobin Yvon "SPEX" Spectrometer Fluoro-MAX-3 or a Nalco TRASAR®350 on-line Fluorometer.

The 2 ppm resazurin solution is put into a 60 ml container from which a pump is used to withdraw the 2 ppm resazurin solution through various tubing, tubing connectors, flow channel or any type of devices for fluid flow.

The 2 ppm resazurin solution is also put into a 60 ml syringe from which the 2 ppm resazurin is injected also into various tubing, tubing connectors, flow channel or any type of devices for fluid flow.

The pump used is a high pressure pump that can deliver up to 6000 psig. The difference between the two modes of delivery, one by a pump and one by a hand-syringe is the difference in pressure capability. In this example, there is also a difference in pumping time between use of the pump and use of the syringe. Approximately 10 to 60 ml of the 2 ppm resazurin solution is pumped for each analysis.

In this Example, the following Samples were prepared and tested:

Throughout this description of samples the following is true: Whenever a pump is used, 60 ml of 2 ppm reagent is pumped at 3 ml/min for 20 minutes.

Whenever a syringe is used to wet the surfaces, 20 ml of reagent is injected taking about 30 seconds.

The internal volume of the entire assembly is approximately 5 ml. Some parts are as small as 0.5 ml volume.

The measurement of the fluorescent signal is made on the following samples:

SAMPLE A—A 40 ppb Resazurin solution is made from the 2 ppm solution using laboratory glassware. This is the standard representing the base-line of no microbial activity.

SAMPLE B—60 ml of the 2 ppm resazurin solution is pumped through a total of six assemblies of flow channel all connected together. The 2 ppm solution that has been pumped through is collected and a portion of this is diluted to 40 ppb using laboratory glassware.

SAMPLE C—An aliquot of 2 ppm resazurin solution is withdrawn with a pipette from the 60 ml container and a 40 ppb solution is made using laboratory glassware.

The six assemblies of equipment (used in SAMPLE B) are disconnected into six separate assemblies, and through each one is pumped by the pump or by a hand-syringe approximately 10 to 30 ml of the 2 ppm resazurin solution. Each of the 2 ppm solution that has been pumped through each assembly is collected and a portion of this is diluted to 40 ppb using laboratory glassware.

SAMPLE D—20 ml of the 2 ppm resazurin solution is passed through a 20 inch long ⅛" stainless tubing with a ball valve at the end.

SAMPLE E—60 ml of the 2 ppm resazurin solution is passed from the pump inlet and collected at the outlet immediately.

SAMPLE F—20 ml of the 2 ppm resazurin solution is passed through a 24 inch long ¼" Tygon tubing which is the tubing used to connect between the 60 ml container and the pump inlet.

SAMPLE G—60 ml of the 2 ppm resazurin solution is passed through another pump and through a 30 inch ⅛" stainless tubing and a ball valve.

SAMPLE H—30 ml of the 2 ppm resazurin solution is passed through a 2 inch long ⅛" stainless steel tubing and a T-connector.

SAMPLE I—An aliquot of the 2 ppm resazurin solution is injected from the hand-syringe into a typical plastic bottle which is used to collect the solution that has been passed through the various devices.

SAMPLE J—The 2 ppm resazurin solution is passed through a check valve using the pump.

SAMPLE K—The 2 ppm resazurin solution is pumped through the same six assemblies under pressure and mixed with the stock solution which is pumped through another pump through a laboratory scale reverse osmosis membrane cell, to a final concentration of 40 ppb is measured on the TRASAR®350 fluorometer.

SAMPLE L—Another source of a 2 ppm resazurin solution, that is stabilized with 0.4 ppm Kathon® (this is a mixture of isothiazolones that is commercially available) is pumped through the same six assemblies under pressure and mixed with the stock solution which is pumped through another pump through a laboratory scale reverse osmosis membrane cell, to a final concentration of 40 ppb is measured on the TRASAR®350 fluorometer.

SAMPLE M—This 2 ppm resazurin solution, with 0.4 ppm Kathon®, is diluted to 40 ppb using laboratory glassware. In the following table, Example Table 2-1 583 refers to the measured fluorescent signal at 583 mini, which is the emission wavelength for resorufin and 634 refers to the measured fluorescent signal at 634 nm, which is the emission wavelength for resazurin. Ratio means the ratio of measured fluorescent signals at 583(resorufin) to 634 (resazurin).

TABLE 2-1

| Description | TRASAR® 350 Fluorometer | | | Fluoro-MAX 3 Fluorometer | | |
|---|---|---|---|---|---|---|
| | Ratio $R_f/R_z$ | $R_f$ at 583 nm | $R_z$ at 634 nm | Ratio | 583 | 634 |
| A Base line of reagent | 0.78 | 30 | 38 | 0.75 | 12685 | 16980 |
| B Entire assembly | 1.20 | 54 | 40 | 1.10 | 21325 | 19465 |
| C Container | 0.80 | 29 | 38 | 0.72 | 13350 | 18570 |
| D Rigid tubing | | | | 0.76 | 15890 | 21020 |
| E Pump | | | | 0.73 | 16090 | 22100 |
| F Flexible tubing | | | | 0.76 | 18220 | 23860 |
| G Second pump & line | | | | 0.79 | 16930 | 21360 |
| H Connector | | | | 0.69 | 15200 | 22090 |
| I Syringe and container | | | | 0.72 | 15740 | 21890 |
| J Check valve | | | | 1.05 | 24845 | 23725 |
| K Entire assembly & membrane | 1.35 | 60 | 46 | 1.18 | 23955 | 20330 |
| L Entire assembly & membrane unit with reagent of different source | 1.60 | 126 | 79 | | | |

TABLE 2-1-continued

| | TRASAR ® 350 Fluorometer | | | Fluoro-MAX 3 Fluorometer | | |
|---|---|---|---|---|---|---|
| | Ratio | $R_f$ at | $R_z$ at | | | |
| Description | $R_f/R_z$ | 583 nm | 634 nm | Ratio | 583 | 634 |
| M Base line of reagent of different source | 1.25 | 88 | 70 | 1.01 | 25485 | 25175 |

The interpretation of these results shows that the microorganisms present in the entire system (entire assembly) can be isolated to the check valve, because the ratio of the fluorescent signals is highest at the check valve.

Example 3

A brewery has eight pasteurizers. The pasteurization process is used to inactivate microorganisms within the beer and prolong the product shelf life. The pasteurizers use water to heat the packaged beer and hold it at a certain temperature for a period of time. The level of heat treatment is typically expressed using pasteurization units, where one pasteurization unit (PU) means pasteurizing beer at 60° C. for one minute. In practice, the beer at this facility is pasteurized using 22–25 PU. The pasteurizers at this facility have a variety of capacities, ranging from 18,000 to >30,000 bottles or cans per hour (bph).

The pasteurizers are made of stainless steel and are double-floor machines. The conveyor belts are made of plastic. Bottles or cans are automatically arranged at the machine inlet across the entire width of the conveyor belt and move through pre-heating, pasteurization, and cooling zones within the pasteurizer. The circulation pumps and spray nozzles within the pasteurizer zones sprinkle the bottles or cans with water circulating in the tanks. Water tanks for the zones are heated with steam or cooled with a cooling tower. A separate nozzle system is used on either floor so that the pasteurization effect on both floors is equal.

A diagnostic test is performed on the pasteurizer water to determine the volume of each zone within the pasteurizers. Pasteurizer number seven is analyzed using the fluorescent tracer 1,5-napthalenedisulfonic acid (TRASAR®I) and a portable fluorometer available from Ondeo Nalco Company, Naperville, Ill. 60563. From this study, the volume of each zone within pasteurizer number seven is determined. The volume (expressed in gallons) of each zone is shown in Table 3-1.

TABLE 3-1

| Z1 | Z2 | Z3 | Z4 | Z5 | Z6a | Z6b | Z7 | Z8 | Z9 | Z10 |
|---|---|---|---|---|---|---|---|---|---|---|
| 1288 | 1030 | 1256 | 1073 | 1145 | 830 | 818 | 1073 | 1256 | 1051 | 1392 |

The pasteurizer construction makes it possible to dose chemicals for adjusting water hardness, corrosively, and for inhibiting the growth of microorganisms. The volume of chemical required for treatment is determined in part by the water volumes determined by the diagnostic TRASAR®study. In spite of this regular chemical addition, microorganisms including bacteria, fungi, and protozoa flourish within the pasteurizer water system. Conditions within the pasteurizer are favorable for microbial proliferation because temperatures are within a range that allow growth (30–50° C.), and nutrients are readily available from spilled beer and oils from the machinery.

Due to a variety of operational and mechanical issues, each pasteurizer is periodically taken off-line. At this time, the pasteurizer is drained and maintenance is performed on the packaging lines. Prior to draining the pasteurizer, it is common practice to treat the pasteurizer water with chlorine bleach to kill microorganisms within the system. This treatment is effective at killing some microorganisms but is insufficient to remove most of the deposits that accumulate within the pasteurizer. This becomes evident when the pasteurizer is returned to service. When restarted, large quantities of biological masses that resemble oatmeal and phlegm become visible within the water. These deposits which originated from hidden portions of the systems clog pipes, valves, and spray nozzles that are not readily available for inspection. This causes operational problems, and is also unacceptable for health and safety reasons.

To prevent this from occurring, the brewery implements a method for determining when biological fouling is present in hidden parts of the system after the pasteurizer has been drained. To detect hidden microorganism-contaminated surfaces, the brewery uses a fluorogenic reagent which is fluorochrome-protein conjugate {eosin-bovine serum albumin (hereinafter "E-BSA")}. The E-BSA reagent is selected based on the ability to detect protease activity from microbial communities within the system, and E-BSA reagent stability to chlorine residuals that remain within the pasteurizer system even after draining.

{The E-BSA reagent is previously synthesized by adding 600 milligrams of bovine serum albumin, 250 milligrams of potassium carbonate, and 150 milligrams of eosin 5-isothiocyanate to 30 milliliters of water. The bovine serum albumin (CAS Number 9048-46-8), potassium carbonate (CAS Number 584-08-7), and eosin 5-isothiocyanate (synonym: EITC) (CAS Number 60520-47-0) are ordered from Sigma-Aldrich Corporation, St. Louis, Mo., USA. The mixture is allowed to react at room temperature, in the dark, over the weekend. Following this reaction period, the E-BSA product is purified to remove free EITC by size exclusion chromatography (gel filtration) using Sephadex G-25 Fine gel filtration media ordered from Sigma-Aldrich Corporation, St. Louis, Mo., USA. Approximately 70 milliliters of E-BSA purified reagent is made using this procedure.}

After the pasteurizer water is treated with chlorine bleach and drained, a sample of the E-BSA reagent is diluted 50,000-fold in tap water. This dilute E-BSA reagent is added to the pasteurizer. The volume of the dilute E-BSA solution is less than that of the typical water volume used in the pasteurizer. The dilute E-BSA is added to the pasteurizer through the piping system and spray nozzles that are used during normal operation of the pasteurizer. By using these same spray nozzles, contact of the dilute E-BSA reagent with surfaces of the system that are wetted during normal operation is assured.

The dilute E-BSA reagent is added to the entire pasteurizer, or to individual parts. For example, it is possible to obtain useful information if only certain zones are analyzed with the dilute reagent. Since some zones have a history of heavier microbial fouling, primarily due to temperature conditions, this targeting of the analysis allows efficient use of the E-BSA dilute reagent, and provides results that determine the location of the microorganisms within the system. Additionally, use of E-BSA reagent allows the detection of hidden microbiological contaminants that are not readily accessible for visual inspection. Because the pasteurizers are double floor models, there are parts of each zone and the conveyor assembly that are difficult to access for visual inspection. The plumbing system of the pasteurizer also has many pipes, valves and pumps. For these hidden areas, the E-BSA dilute reagent is the simplest available method for detecting microorganisms.

After the dilute E-BSA reagent is added to the system, it is collected from the tank for each zone. The samples are analyzed by measuring the fluorescence within each sample. Fluorescence is measured using a fluorometer (SPEX FluoroMax-2 fluorometer available from Jobin Yvon Spex, 3880 Park Ave, Edison N.J. 08820) with excitation at 521 nm, emission at 537 nm and slit widths of 3.0/3.0. The fluorescence is 12,100 prior to exposure to the pasteurizer system. Following exposure to the system, the measured fluorescent signal of the dilute E-BSA reagent is as shown in Example Table 3-2. In Example Table 3-2, the Exposure Time is reported in Minutes and the heading Fluorescence refers to the measured fluorescent signal of the E-BSA at the indicated time.

EXAMPLE TABLE 3-2

| Exposure Time | Fluorescence |
| --- | --- |
| 0 | 12100 |
| 10 | 16890 |
| 20 | 25650 |
| 30 | 32970 |
| 40 | 36300 |
| 50 | 40010 |
| 60 | 43090 |
| 90 | 56430 |
| 120 | 70150 |
| 180 | 100530 |

Example Table 3-2 shows a rate of 491 fluorescent units/minute for a 180 minute exposure time. This rate is calculated using the formula (measured fluorescent signal at 180 minutes minus the measured fluorescent signal at time zero)/(180 minutes−0 minutes)=(100,530−12,100)/(180−0)=491 fluorescent units/minute. For the clean pasteurizer, the rate is also determined at 180 minutes and the rate =(24,160−12,100)/(180−0)=67 fluorescent units/minute.

The rate of increase in the measured fluorescent signal of the dilute E-BSA reagent is proportional to the quantity of microbial fouling within the drained pasteurizer system where the E-BSA dilute reagent is applied. Example Table 3-2 shows a rate of 491 fluorescent units/minute for a 180 minute exposure time. This is compared to a rate of 67 units/minute for a 180 minute exposure time in a "clean" pasteurizer with no hidden microorganisms.

This particular facility uses a rate of 200 fluorescent units per minute as the trigger level for additional cleaning. By using the method of the instant claimed invention, this heavy-duty mechanical and chemical cleaning process is targeted to the part of the system that needs it most. The ability to "target" the heavy duty cleaning to only that section of the industrial water system is highly desirable as heavy duty cleaning involves the use of high chlorine levels and detergent, it is expensive and time consuming because it involves overtime work by brewery employees or the hiring of a cleaning company, and in addition, heavy duty cleanings may be corrosive to the pasteurizer metals, and can extend the amount of pasteurizer down-time.

At 30,000 bph for each pasteurizer, the brewery cannot afford to have a pasteurizer down for the time required to perform heavy duty cleanings unless the E-BSA dilute reagent testing method verifies the need for the heavy duty cleaning. Once the E-BSA method is adopted by the brewery, the brewery decreases the heavy duty cleaning frequency for zones within several of the can pasteurizers and also increases the frequencies of cleanings in several problematic areas within each pasteurizer. These improvements save the brewery several thousand dollars each year in cleaning costs, and allow easier pasteurizer start-ups mostly free from the biological masses that once caused operation problems and decreased productivity. For those pasteurizers that have undergone heavy duty cleaning, the E-BSA dilute reagent method is also used to verify the efficacy of the heavy duty cleaning. These results are documented and are used by brewery operations management to demonstrate due diligence in maintaining sanitary packaging conditions within the brewery.

Although the invention has been described in detail for the purpose of illustration, it is to be understood that such detail is solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

What is claimed is:

1. A method for locating hidden microbial deposits on water contact surfaces of industrial water systems comprising the steps of:

a) providing an industrial water system;

b) draining the water from said industrial water system, or in the alternative, from a targeted portion of said industrial water system;

c) applying a solution or dispersion of a fluorogenic reagent in water to the water contact surfaces of said industrial water system and allowing said fluorogenic reagent to react with any hidden microbial deposits present, wherein said fluorogenic reagent is selected from the group of fluorogenic reagents that are known to react with microbial deposits such that a fluorescent signal of said fluorogenic reagent is detectable in such a way as to make the detection of the fluorescent signal indicate that there are hidden microbial deposits present on the water contact surfaces of the equipment and piping;

d) collecting said solution or dispersion after it has been in contact with the hidden microbial deposits on water contact surfaces of said industrial water system;

e) providing means for measurement of the fluorescent signals of said fluorogenic reagent in the collected solution or dispersion;

f) using said means for measurement as set forth in step e of said fluorescent signals of said fluorogenic reagent to measure the fluorescent signal of the fluorogenic reagent; and g) using the measured fluorescent signal to determine whether hidden microorganisms deposits are present on the water contact surfaces of the equipment and piping of the industrial water system.

2. The method of claim 1, wherein the location of the hidden microbial deposits on water contact surfaces of industrial water systems is determined; further comprising the step of h) moving the application point for the solution of fluorogenic reagent and the collecting point for the solution after it has been in contact with the water contact surfaces of interest and repeating steps c), d), e), f) and g) as necessary in order to determine whether there are hidden microbial deposits on the water contact surfaces of interest and if there are hidden microbial deposits present, locating where they are in the industrial water system.

3. The method of claim 1, wherein said fluorogenic reagent is selected from the group consisting of fluorogenic reagents that have a fluorescent signal; wherein said fluorescent signal changes after said fluorogenic reagent comes into contact with microorganisms.

4. The method of claim 3, wherein said fluorogenic reagent is selected from the group consisting of resazurin, resazurin, sodium salt, 4-methylumbelliferyl phosphate and pyranine phosphate.

5. The method of claim 1, wherein said fluorogenic reagent is selected from the group consisting of fluorogenic reagents that have a low level fluorescent signal; wherein the low level fluorescent signal of said fluorescent reagents increases after said fluorescent reagents come into contact with microorganisms.

6. The method of claim 5, wherein said fluorogenic reagent is selected from the group consisting of fluorochrome-polysaccharide conjugates.

7. The method of claim 5, wherein said fluorogenic reagent is selected from the group consisting of fluorochrome-protein conjugates.

8. The method of claim 1, wherein said fluorogenic reagent is selected from the group consisting of fluorogenic reagents that have a detectable fluorescent signal; wherein the detectable fluorescent signal decreases after said fluorogenic reagent comes into contact with microorganisms.

9. The method of claim 8, wherein said fluorogenic reagent is, Rhodamine Green.

10. The method of claim 1 in which an inert tracer is added in a known concentration to the solution or dispersion of fluorogenic reagent.

11. The method of claim 3 in which an inert tracer is added in a known concentration to the solution or dispersion of fluorogenic reagent.

12. The method of claim 5 in which an inert tracer is added in a known concentration to the solution or dispersion of fluorogenic reagent.

13. The method of claim 8 in which an inert tracer is added in a known concentration to the solution or dispersion of fluorogenic reagent.

* * * * *